United States Patent [19]
Hedner et al.

[11] Patent Number: 6,034,117
[45] Date of Patent: Mar. 7, 2000

[54] METHODS OF TREATING AND DIAGNOSING SLEEP DISORDERED BREATHING AND MEANS FOR CARRYING OUT THE METHOD

[76] Inventors: Jan Hedner, Orangerigatan 4, S-412 66 Göteborg; Holger Kraiczi, Viktoriagatan 34, S-411 25 Göteborg, both of Sweden

[21] Appl. No.: 09/091,382
[22] PCT Filed: Dec. 17, 1996
[86] PCT No.: PCT/SE96/01677
§ 371 Date: Sep. 21, 1998
§ 102(e) Date: Sep. 21, 1998
[87] PCT Pub. No.: WO97/22339
PCT Pub. Date: Jun. 26, 1997

[30] Foreign Application Priority Data

Dec. 19, 1995 [SE] Sweden .................................. 9504537

[51] Int. Cl.[7] .......................... A61K 31/40; A61K 31/27; A61K 31/44; A61K 31/165; A61K 31/55
[52] U.S. Cl. .......................... 514/411; 514/490; 514/351; 514/620; 514/642; 514/335; 514/483; 514/643; 514/297; 514/141; 514/114; 514/365; 514/353; 514/229.8; 514/215; 514/221
[58] Field of Search ..................... 514/490, 411, 514/351, 620, 642, 335, 483, 643, 297, 141, 114, 365, 353, 229.8, 215, 221

[56] References Cited

U.S. PATENT DOCUMENTS 5,298,504  3/1994  Sommer et al. ........................ 514/221

OTHER PUBLICATIONS

Rupreht et al, Medline Abstracts, abstract No. 90000187, 1989.

Guilleminault et al, Embase Abstracts, abstract. No. 74009132, 1973.

*Primary Examiner*—William R. A. Jarvis
*Attorney, Agent, or Firm*—Hopgood, Calimafde, Kalil & Judlowe, LLP

[57] ABSTRACT

This invention relates to a method for treating snoring, sleep apnea and other form of sleep-disordered breathing, which comprises administration of a therapeutically effective dose of an acetyl choline esterase inhibitor (CEI) such as pyridostigmine or a pharmaceutically acceptable salt thereof.

20 Claims, 1 Drawing Sheet

METHODS OF TREATING AND DIAGNOSING SLEEP DISORDERED BREATHING AND MEANS FOR CARRYING OUT THE METHOD

This application is a 371 of PCT/SE96/01677, filed Dec. 17, 1996.

FIELD OF THE INVENTION

The present invention relates to a method of treating and diagnosing snoring, sleep apnea and other forms of sleep disordered breathing, and to a means for carrying out said method.

BACKGROUND OF THE INVENTION

A basic requirement for breathing is the patency of the upper airway. This, of course, also holds true for breathing during sleep. It has recently been described that such patency—and thus breathing—may be partially or totally interrupted during sleep due to a collapse or obstruction of the upper airway; it should be observed that obstruction, in the context of the present invention, excludes obstruction by foreign objects or by material excreted by the body, such as mucus. In its simplest form partial upper airway collapse or obstruction is indicated by profound and vigorous snoring. More pronounced collapse or obstruction results in hypopnea, a condition in which airflow is reduced during inspiration with or without concomitant signs of hypoxemia. The condition of total collapse of the upper airway is referred to as obstructive sleep apnea (OSA). This condition is associated with repeated episodes of interrupted airflow in spite of inspiratory attempts, resulting in hypoxemia, hemodynamic changes and arousal from sleep. Sleep fragmentation, hypoxemia and/or other OSA-associated phenomena yet unidentified are likely to lead to typical daytime symptoms including hypersomnolence, cognitive disturbance, reduced working and driving performance, depression, and loss of memory. Moreover, cardiovascular complications, in particular hypertension, cardiac failure, myocardial infarction, and stroke have been associated with OSA. Such symptoms and complications are not confined to severe cases but also observed in cases of partial OSA.

The prevalence of OSA in the adult male population is in the order of 10–12%. The prevalence of OSA in combination with pronounced daytime symptoms is in the order of 1–3%. The prevalence of minor daytime symptoms induced by discrete sleep-related breathing disturbances is unknown. However, habitual snoring is a common phenomenon reported by 15–25% of the adult population.

The pathophysiology of OSA is virtually unknown. Though a number of predisposing factors have been identified, e.g. obesity, hypertrophied tissue in the upper airway (particularly in children), and short jaw, there is a large number of OSA-prone individuals lacking these factors.

The absence of observable aberrant anatomic factors, however, does not exclude a dynamic malfunction of the tongue and the upper airway dilating musculature. Such defects function may originate in the central nervous system, at the level of signal transmission to peripheral muscles or at the neuromuscular junction. It is well known and has been reported in literature that electromyographically recorded signals from the lingual muscles (submental EMG) may be attenuated or even disappear in association with obstructive apnea. This defective control seems to be particularly pronounced during sleep only, suggesting that central nervous, peripheral neural and/or neuromuscular control of the upper airway is particularly prone to be affected in this state.

The principal forms of treatment in OSA are surgery of the upper airway, intraoral mandibular advancement devices and long-term treatment with nasal continuous positive airway pressure (nCPAP). These methods of treatment are cumbersome and expensive. Various forms of pharmacological treatment, e.g. by administration of tricyclic antidepressants, theophylline, progesterone, have been employed but have not gained wide clinical use.

OBJECTS OF THE INVENTION

As evident from the preceding description of the state of the art, there is a need for an improved method for treating snoring, sleep apnea and other forms of sleep disordered breathing. In particular, pharmacological treatment of such disorders would offer a definite advantage over of the invasive or non-invasive methods used at present, many of which only provide insufficient relief and some of which are cumbersome to the patient.

One object of present invention thus is to provide a method for the treatment of snoring, sleep apnea and other forms of sleep disordered breathing which reduces and/or eliminates some or all of the drawbacks of the methods known in the art. Another object of the present invention is to provide a means for carrying out said method according to the invention. A further object of the present invention is its application as a diagnostic tool for detecting the presence of OSA in a patient.

SUMMARY OF THE INVENTION

According to the present invention there is provided a method of treating snoring, sleep apnea and other forms of sleep disordered breathing, all of them which included in the term OSA as used herein, said method comprising the administration of a pharmacologically active amount of an agent having an inhibitory effect on acetylcholine esterase, that is, a so-called acetylcholine esterase inhibitor. For the sake of simplicity, acetylcholine esterase inhibitors will be referred to as choline esterase inhibitors (CEI) in the present application.

DETAILED DESCRIPTION OF SPECIFIC EMBODIMENTS

Figure 1:
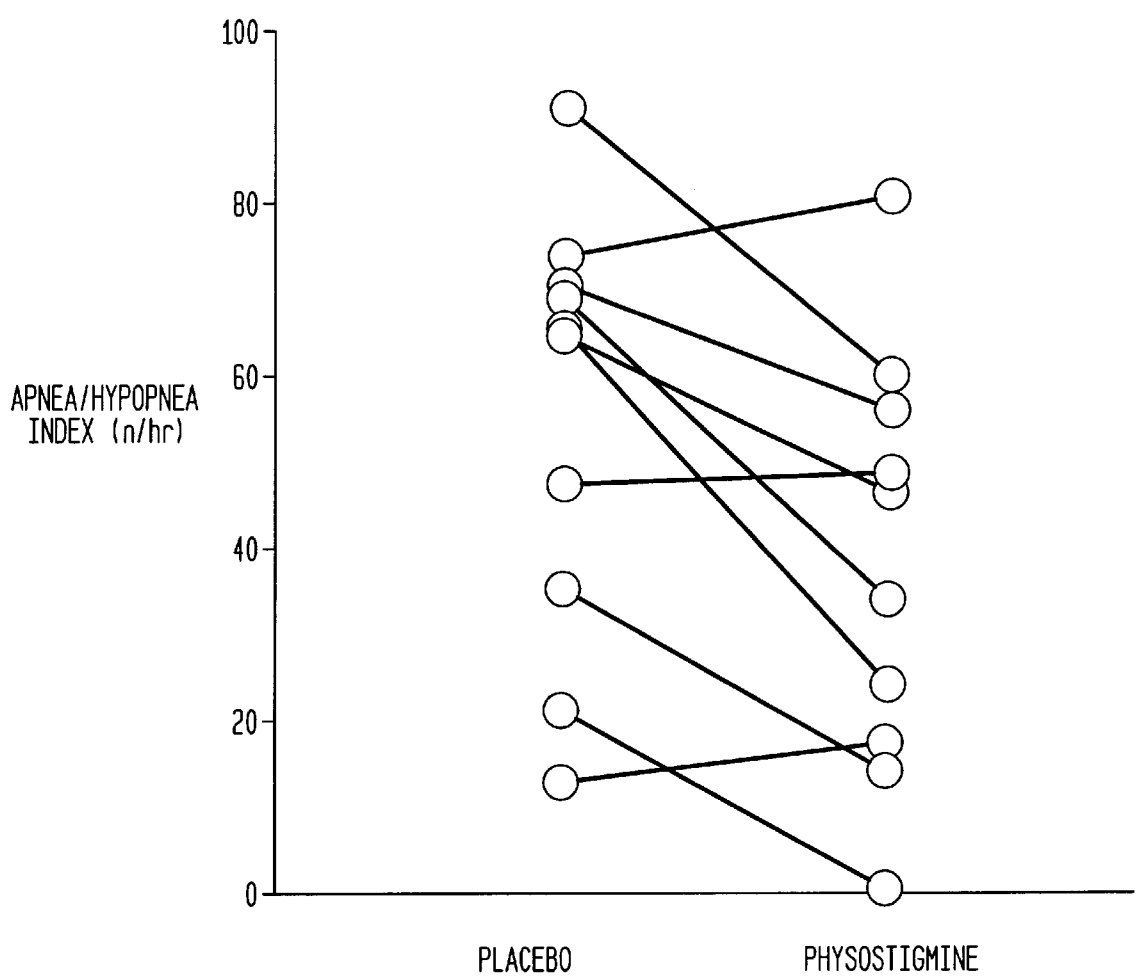
FIG. 1 shows placebo versus physiostigmine effects in each patient subjected to a double-blind study.

For many years CEI have been used in medicine for the treatment of a number of diseases and abnormal conditions but not for the treatment of snoring, sleep apnea and other form of sleep disordered breathing.

The known use of CEI has resulted in the gathering of substantial clinical experience specific to choline esterase inhibitors. Known medical indications in which CEI are or have occasionally been used as medicines include intestinal and bladder atonia and myasthenia gravis. In addition, CEI of various structure are widely employed as antidotes to clinically used muscle relaxant agents, in particular curare. For a recent survey in respect of known therapeutic uses for CEI, see: P Taylor, Anticholinesterase Agents, in Goodman and Gilman's *The Pharmacological Basis of Therapeutics*, 8th Ed., Pergamon Press, N.Y. etc., 1990.

The positive effect of CEI in the treatment of OSA-related conditions may be due to the enhancement of cholinergic transmission at the level of the neuromuscular junction or, possibly, in the nervous system, causing increased muscular tone in upper airway muscles during sleep and thereby reducing snoring, sleep apnea and other forms of sleep disordered breathing (OSA). While this hypothesis provides a scientifically attractive explanation for the observed effect of said CEI in the conditions which the present invention seeks to treat, it must be emphasized that it must not be considered to be binding in any way on the concept and the working of the present invention. Central nervous acetylcholinergic mechanisms are intimately involved in the regulation of wakefulness and sleep, particularly rapid eye movement (REM) sleep. Particularly interesting anatomic structures containing cholinergic nerve cells include the dorsal pontine tegmentum, the thalamus, the cerebral cortex and the hippocampus (see Tononi and Pompelano, Pharmacology of the cholinergic system. In: The Pharmacology of Sleep, Ed. A. Kales, Springer Verlag, Berlin 1995, pp 143–210). In humans, systemic administration of CEIs can produce an increase in REM sleep and a shortening of the latency from sleep onset to the first episode of REM sleep. Infusion of the CEI physostigmine was also shown to reduce sedation and induce arousal in the postoperative phase in patients exposed to major surgical intervention. The effect of CEI on central respiration related mechanisms is less well characterised. Previous published data suggest that cholinergic activation, similar to that seen during natural REM sleep, is associated with a predominant inhibition of upper airway (hypoglossal) activity in animal experimental models. Such an effect would advocate an increased tendency to upper airway collapse during sleep and increased acetylcholinergic tone. An attractive hypothesis for the observed effect of said CEI may therefore be that the central nervous control of upper airway muscles is profoundly modified in certain disease states such as sleep disordered breathing, a state actually associated with a suppression of the natural progression of sleep, in particular REM sleep and slow wave sleep. Further indirect support for such an interpretation would be that the observed effects were not confined to REM sleep periods but were also seen during non-REM sleep.

An effective amount of a CEI (or a combination of several CEI) is one which eliminates or substantially reduces the manifestations of OSA-related conditions over a period of sleep, such as sleep periods from 10 minutes to 10 hours.

Many agents inhibiting the effect of choline esterase are known in the art. Their chemical structure may vary considerably. CEI particularly useful in the invention include synstigmine, neostigmine, physostigmine, pyridostigmine, ambenon (ambenonium), distigmine, demecarium, neostigmine, edrophonium, tacrine (9-amino-1,2,3, 4tetrahydroacridine), metrifonate, ecothiopate, eptastigmine, tetrahydrobenzazepine and its alkylcarbamate derivatives, amiridine, linopidine, ENA-713 (a proprietary compound of Sandoz AG in clinical study for the treatment of Alzheimers disease), velnacrine (a compound in clinical study for the treatment of Alzheimers disease), C1-INH (a regulatory glucoprotein having CEI activity), thiabendazole, mitezol, 3,4-diaminopyridine, eseridine, and galantamide, including pharmaceutically acceptable salts of those of the aforementioned compounds which are able to form salts with organic or inorganic acids. The aforementioned compounds are fully described in the literature; see, for instance: *Therapeutic Drugs*, C Dollery, Ed., Churchill Living-stone, Edinburgh etc., 1991, and references cited therein. In this publication, which is hereby incorporated by reference, pharmaceutical compositions useful in the invention are described for a number of CEI.

Other CEI useful in the invention include arisugacin; 5,7-dihydro-3-(2-(1-(phenylmethyl)-4-piperidinyl)ethyl)-6H-pyrrolo(3,2-f)-1,2-benzisoxazol-6-one; pseudozoanthoxanthin; aminostigmine; atramine; B 156; chinotilin; crotylsarin; Cui xing an; Cui xing ning; cycloguanide phenylsulfone; cyclophostin; diethyl mesoxalate; diethyl S-n-propyl phosphorothiolate; diisopropylamine dichloracetate; diisopropyl-phosphorylthiocholine iodide; dimethylcarbamyl fluoride; dimethyl-carbamylcholine; dimethylthionocarbamylcholine; E 2020; EGYT 2347; ENA-713; ethyl 4-nitrophenyl methylphosphonate; fasciculin; fordine; GA 95; GD 7; GT 161; GT-165; hexafluorenium; hexamethylenebis (dimethyl-(3-phthalmidopropyl) ammonium bromide); hexyl 2,5-dichlorophenylphosphoroamidate; HSR 803; huperzine A; huperzine B; huperzinine; indolinyl-N,N-dimethylcarbamate; isopropyl S-2-trimethylammoniumethylmethylphosphonothioate; KW 5092; LG 63; methacyne; methanesulfonyl fluoride; methylphosphonfluoridate; methylphosphonothiolate; methylsulfomethylate; myotol; N-(ε-aminocaproyl)-p-aminophenyltrimethylammonium; N-demethylhuperzinine; N-methylhuperzine B; N-methylpiperidine; N,N-dimethylcarbamic acid 2,3-dihydro-1,3,3-trimethylindol-5-yl ester; N,N'-diisopropylphosphorodiamidic anhydride; nibufin; normeperidine; norneostigmine; norpyridostigmine; O-(3-(trimethylammonium)phenyl)-1,3,2-dioxaphosphorinane 2-oxide; O-ethyl N,N-dimethylamino-S-(2-diethylaminoethyl)thiophosphate; O-ethyl O-4-nitrophenyl phosphoramidate; O-methyl-S-n-hexylmethylthiophosphonate; onchidal; PD 142676; phlegmariurine C; physostigmine heptyl; physostigmine methiodide; pinacolyl S-(2-dimethylaminoethyl) methylphosphonothioate; pinacolyl S-(2-trimethylaminoethyl)methylphosphonothioate; PK-154, pyridostigmine; quinolytin; RA 7; Ro 20683; Ro 46-5934; RX 67668; RX 72601; S-(2-(diethylamino)ethyl) alpha-keto-4-methylbenzothiohydroximate; S-(2-(diethylamino) ethyl) 4-methylbenzothiohydroximate; S-methylmethylparathion; sanguiritrine; SM 1088; stephaglabrine; territrem B; tetraethyl pyrophosphate; tetrahydropyridostigmine; THB 013; tripropylammonium; VX; zifrosilone; 1-(2-methyl-6-benzothiazolyl)-3-(N-benzyl-4-piperidinyl) propan-1-one; 1-(3,4-(methylenedioxy)benzyol)-3-(2-(1-benzyl-4-piperi-dinyl)ethyl)-thiourea; 1-benzyl-4-(2-(N-[4'-(benzylsulfonyl)benzoyl]-N-methyl aminoethyl)piperidine; 1-bromopinacolone; 1-methyl-S-(3-methylthiophosphoryl) imidazolium; 1,3,2-dioxaphosphorinane-2-oxide; 1,5-bis(4-trimethylammoniumphenyl)pentan-3-one; 2-(methylsulfonyl)ethanol; 2-(trimethylsilyl)ethanol; 2-(trimethylsilyl)ethyl acetate; 2-(trimethylsilyl)methyl acetate; 2-dimethylaminoethyl-(dimethylamido) fluorophosphate; 2-heptyl-2-nitrophenylmethylphosphonate; 2-hydroxymethyl-N,N-dimethylpiperidinium; 2-hydroxytacrine; 2-isopropyl-S-(2-diisopropylaminoethyl)methylthiophosphonate; 2-N,N-dimethylaminomethyl-5-methylfuran; 2'-heptylcarbamoyloxy-2-methyl-6,7-benzomorphan; 217A0; 3α,17β-dibutyryloxy-2 beta, 16β-dipiperi-dino-5α-androstane dimethobromide; 3-(N,N-dimethylamino) trifluoroacetophenone; 3-(2-methoxyphenyl)-5-methoxy-1, 3,4-oxadiazol-2(3H)-one; 3-(2,3-dihydro-2,2-dimethylbenzofuran-7-yl)-5-methoxy-1,3,4-oxadiazol-2 (3H)-one; 3-carbamyl-N-allylquinuclidinium; 3-deoxyvasicine; 3-hydroxy-N,N-dimethylpiperidinium; 3-hydroxymethyl-N,N-dimethylpiperidinium; 3-MPAM-ES; 3,3-dimetyl-2-butyl methylphosphonofluoridate; 3'-chloro-4-stilbazole; 33 SN; 4-azidobretylium tosylate;

4-hydroxy-N,N-dimethylpiperidinium; 4-hydroxytacrine; 4-nitrophenyl methyl (4-trifluoromethylphenyl)-phosphinate; 4-phenylazophenyltrimethylammonium; 5-(1,3,3--trimethylindolinyl)-N-(1-phenylethyl)carbamate; 5-(7-nitrobenz-2-oxa-1,3-diazol-4-yl)aminoethylmethyl-phosphonofluoridate; 51 C; 7-[(methylethoxyphosphinyl)oxy]-1-methylquinolinium; NXX-066; NLA-814; HP-290; and their pharmaceutically salts and esters.

Since the choline esterase inhibiting effect of the compounds of the invention, except for non-ionic compounds, usually resides in the nitrogen base part of the agent, the expert in the art will recognize that the desired pharmacological effect will be retained as long as the structure of the nitrogen base remains essentially unchanged. It is thus possible to combine various pharmacologically acceptable acids with said active bases to obtain CEI agents having have desirable properties from a pharmaceutical formulation standpoint, such as salts being only slightly soluble in aqueous solutions which may of particular interest in the manufacture of controlled release CEI-preparations.

The CEI mixture of such inhibitors is advantageously formulated in a way appropriate to the chosen administration route.

The CEI or mixture of such inhibitors may be administered by various routes. The most preferred route is by peroral administration. In this context the compound of the invention is incorporated in tablets, lozenges, capsules or similar, in particular solid pharmaceutical preparations designed for preferred uptake of the compound through the oral mucosa. Most preferred is absorption within the oral cavity, such as sublingual absorption and, consequently, pharmaceutical compositions adapted to such absorption are of particular interest. Knowledge about clinical pharmacokinetics of CEI (see, for instance: P Hartvig et al., Clinical pharmacokinetics of acetylcholinesterase inhibitors, in *Progress in Brain Research*, 84 (1990), 139–143, including secondary references; S-M Aquilonius et al., Pharmacokinetics and Oral Bioavailability of Pyridostigmine in Man, *Eur. J. Clin. Pharmacol.* 18 (1980) 423–428) is useful in designing CEI preparations for administration to a patient.

For this purpose formulation techniques known in the art may be used; in this context reference is made to Pharmaceutical Dosage Forms: Tablets. Vol. 1–3, H A Lieberman et al., Eds. Marcel Dekker, N.Y. and Basel, 1989–1990, which hereby is incorporated into this application by reference. In particular specific reference is made to chapter 7 (Special Tablets, by J W Conine and M J Pikal), chapter 8 (Chewable Tablets, by R W Mendes, A O Anaebonam, and J B Daruwala), and chapter 9 (Medicated Lozenges; by D Peters). Most CEI are salts of quaternary amines or tertiary amines which may form salts with appropriate organic or inorganic acids. In respect of their incorporations as active ingredients in solid or semi-solid pharmaceutical formulations CEI (as salts) can be expected to possess physical properties similar to other kinds of pharmacologically active agents of quaternary or tertiary amine type, such as, for example, synthetic antimuscarinic agents (clinidinum salts, hyoscine methobromide, orphenadrine hydro-chloride); information in respect of formulation techniques for such known antimuscarinic agents thus is useful in carrying out the present invention (for references, see: Martindale, *The Clinical Pharmacopeita*, 29th Ed., The Pharmaceutical Press, London 1989.

It is also possible to administer the compounds according to the invention by the peroral route in a way in which CEI-absorption will be directed to the gastro-sintestinal tract. Appropriate formulations for this variant are also found in the aforementioned publication.

Since it seems to be particularly attractive to affect, by the choline esterase inhibitor of the invention, the nerves supplying the submandibular triangle, such as the hypoglossal and the glossopharyngeal nerves, slow continuous administration of the compound according to the invention in close proximity to these nerves is preferred, such as sublingual administration. Thereby the CEI will be taken up by the mucosa in the sublingual area and migrate to said nerves to exhibit its choline esterase inhibiting function. It is desirable to design the buccal or sublingual pharmaceutical formulation for sustained release of the choline esterase inhibitor to avoid the need for frequent administration which would be particularly difficult during sleep. A suitable solution for this problem would be the fixation, at least for a certain period of time, of the formulation containing the choline esterase inhibitor in or near the sublingual region. This could be effected by fixation of a holding means for the tablet, lozenge, or similar to one or several teeth of the lower jaw, or by implantation of a holding means, of titanium, for instance, in the lower jaw. Such a holding means could also be used for holding a small plastic or other container enclosing a liquid or solid pharmaceutical composition of the choline esterase inhibitor of the invention, from which container the inhibitor would leak through a minute opening or through a system of micropores driven by, for example, osmotic pressure, such as in the technology for sustained release of drugs developed by Alza Corp. It is also possible to incorporate the compound of the invention in a polymer matrix, biodegradable or not, from which it would leak slowly into the oral cavity. Appropriate technology for producing biodegradable polyester matrices of the polylactide/polyglycolide type for incorporation and sustained release of pharmacologically active compounds is described in, for instance, L A Sanders et al., *J. Pharmaceutical Sci.* 75 (1986) 356–360, and in U.S. Pat. No. 3,773,919 (Boswell). Non-degradable polymers of appropriate physical properties can be also used as matrices.

Other devices of absorbing material specifically designed for this purpose such as sponges, non-woven inlays, pieces of woven tissue, felt or other absorbent material useful for slow-release purposes of the compounds according to the invention may be placed under the tongue thus restraining their displacement, or may be fixed to a mandibular dental frame in a buccal or frontal position. The size and shape of these absorbing devices should be adapted to decrease the risk of displacement and to minimize discomfort. Such adaptation is also necessary to avoid accidental swallowing or aspiration of the device containing the drug. This route of administration ensures a highly localized absorption of the drug by the surrounding tissues affecting the patency of the upper airway and the pharynx during sleep. Moreover, a device of this sort designed for slow release will extend the potential effect of the drug over periods beyond those limited by the basic pharmacokinetic properties of the agent, thereby maximising efficiency and duration of treatment which can be extended to cover the entire sleeping period.

Where applicable, choline esterase inhibitors may be used in form of their racemates or as substantially pure enantiomers. Parenteral administration of the CEI according to the invention is also feasible.

The amount of CEI to be administered for treatment of sleep disordered breathing will vary depending on factors such as the particular chemical nature of the inhibitor used, the route of administration, the release profile of the formulation into which it is incorporated, the severity of the disease, individual pharmacokinetic and -dynamic properties as well as the status of the patient. For instance, the dose range for peroral administration of pyridostigmine will be in the interval from 0.1 to 6,000 mg per 24 hours. An amount of from 0.5 to 2,500 mg of pyridostigmine is envisaged as the normal range used for peroral administration. The appropriate dose range for a particular compound can be determined by titration in routine experiments.

In addition to the methods of administration of the compounds of the invention mentioned above also parenteral, intranasal, and rectal administration is useful, as well as administration by inhalation or transdermal administration, particularly to the skin of the submandibular triangle region.

When given by peroral administration for gastrointestinal absorption or administered by the parenteral or rectal route the drug formulation is intended to provide a systemic effect. Systemic administration, for instance, offers advantages in cases with reduced local absorption capacity or when a generalised effect involving extended muscle groups of the pharynx and the upper airway is preferred. Furthermore, the systemic route of application may be preferable to achieve central nervous effects of the drug, specifically for enhancing the central nervous drive to the upper airway musculature.

The CEI according to the invention can also be efficiently administered by inhalation, such as by inhalation via the mouth or via the nose. The nasal mucosa is easily accessible by use of extra- or intranasal devices, the later ones appropriately shaped and designed similarly to what has been described above for intraoral or sublingual administration. The transdermal route of administration is specifically advantageous in regard of simplicity and from a patient comfort standpoint. In this case, the agent is applied to the skin in form of a viscous ointment or similar. Transdermal systems (patches provided with a liquid or semi-liquid pharmaceutical composition) for controlled drug delivery through the skin are well known in the art, for instance for the administration of nicotine and drugs used for the treatment of diseases of the circulatory system. As already mentioned the site of application of transdermal patches can advantageously be a site in the immediate proximity of the upper airway or tongue musculature, such as submentally, on the cheek, the neck, or over the throat.

The timing of the administration of the composition and/or device comprising a choline esterase inhibiting compound according to the invention will depend on the particular compound, its rate of absorption through the mucosa or the skin, the release profile of the respective sustained release composition and/or device, if used, and similar. Typically, the administration of the CEI will, in the majority of cases, have to start well in advance of the sleeping period to achieve optimal effect, for instance from 10 minutes to 3 hours prior to the onset of sleep.

The CEI according to the invention may also be combined, in one and the same pharmaceutical preparation, with other pharmacologically active compounds useful in the treatment of OSA.

The choline esterase inhibitors according to the invention may also be used for diagnosing sleep disorders related to snoring, sleep apnea or other forms of sleep disordered breathing to dissociate them from other types of sleep disorders. The diagnostic method according to the invention comprises administration to the patient a CEI in increasing amounts prior to or during a series of sleep episodes; administration can be in simple or multiple doses. The observation of a reduction of the severity and/or number of sleep disordered breathing events or reduced daytime sleepiness/increased alertness is indicative of the presence of obstructive sleep apnea.

The invention will now be explained in more detail by reference to a preferred but not limiting embodiment illustrated by a single figure (FIG. 1) showing placebo versus physiostigmine effect in each of the patients.

Double-blind, Placebo Controlled Cross Over Study with Physostigmine Salicylate

A double-blind, placebo controlled cross over study with the CEI physostigmine salicylate was undertaken in 10 patients with moderate to severe obstructive sleep apnea (apnea-hypopnea index, AHI 14–94, number n of episodes/hr). Continuous intravenous infusion (12 $\mu$g/min/kg during 7 hours) of physostigmine salicylate resulted in a mean reduction of AHI of 16.5 (app. 30%). Three patients were non-responders (placebo-physiostigmine salicylate difference in AHI within ±5%) while the remaining 7 patients reduced their AHI between 30% and 63%. The change in total sleep time in the 10 patients during the 7 hour recording ranged between −178 and +34 minutes. There was a significant (p-0.046) negative correlation between the reduction in total sleep time (TST) and the reduction in AHI suggesting that a clinically relevant reduction of sleep time (exceeding 60 minutes) only occurred in patients not responding with a reduction in AHI. No side effects were reported during any of the study nights.

These findings demonstrate a potent apnea effect of a CEI agent in sleep apneics. Moreover this study suggests that the expected negative (arousal inducing) effect of CEI of tertiary amine type may be differentiated from those resulting in an improvement of upper airway patency during sleep.

The study of OSA in animal models or in healthy persons (OSA then being induced by artificial means) may lack relevance for patients in which acetylcholine related dysfunction is genetically determined.

CEI/REM Sleep Suppressing Agent Combination Therapy

It is known that CEI have other effects, in particular systemic effects, than those desired in the context of the present invention. These effects are chiefly due to excessive cholinergic stimulation and include increased salivation, nausea and vomiting, abdominal spasms, muscle cramps, bradycardia, increased bronchal secretion, and diarrhoea. It is within the scope of the present invention to counteract a specific side effect of this kind by administration of an agent known in art to be effective in its suppression, for instance an antidiarrhoeal agent, such as loperamide hydrochloride and lidamine hydrochloride, in case of diarrhoea, or an anti-vomiting agents, such as domperidone, in case of nausea and vomiting.

An improved effect of administration of CEI according to the invention can be expected when the medicine is given in combination with an agent capable of counteracting unwanted CEI effects, including an agent for deep sleep promotion, in particular an REM sleep suppressing agent. Such REM sleep suppressing agents are known in the art and include but are not limited to tricyclic antidepressants, selective serotonin reuptake inhibitors, bensodiazepines, cyclopyrrolones, and antihistamines. Examples for such agents are amitriptyline hydrochloride or embonate, fluoxetine, imipramine hydrochloride, mianserin hydrochloride, nortryptiline hydrochloride, paroxetine hydrochloride, phenelzine sulphate, protriptiline hydrochloride, tranylcypromine sulphate, trimipramine maleate, viloxazine hydrochloride, alpraxolam, chlormethiazole edisylate, chlorpromazine hydrochloride, diazepam, droperindol, fluphenazine decanoate, flurazepam hydrochloride, gluthethimide, haloperindol decanoate, lorazepam, meprobamate, nitrazepam, oxazepam, pentobarbitone, pericyazine, pimozide, prochlorperazine mesylate, quinalbarbitone sodium, sulpiride, thioridazine hydrochloride, triazolam, trifluoperazine hydrochloride, zopiclone, zaleplone, solpidem, diphenhydramine, doxylamine succinate, and promethazine hydrochloride.

For administration of the CEI in combination with a deep sleep promoting agent, in particular an REM sleep suppressing agent, a pharmaceutical composition containing both of them can be used or they can be administered in separate pharmaceutical compositions simultaneously or consecutively. Consecutive administration is preferred for pharmacokinetic reasons, such as for proper timing of the onset of effect caused by the respective agent. For this purpose sustained or delayed release compositions are preferred.

It is claimed:

1. A method for treating snoring, sleep apnea and other forms of sleep disordered breathing, comprising administration to a patient of a therapeutically effective dose of an acetyl choline esterase inhibitor (CEI) over an appropriate period of time substantially coinciding with the period of sleep of said patient.

2. The method of claim 1, wherein the CEI is selected from synstigmine, physostigmine, pyridostigmine, ambenon (ambenonium), distigmine, demecarium, neostigmine, edrophonium, tacrine (9-amino-1,2,3,4-tetrahydroacridine), metrifonate, ecothiopate, eptastigmine, tetrahydrobenzazepine and its alkylcarbamate derivatives, amiridine, linopidine, ENA-713, velnacrine, C1-INH, thiabendazole, mitezol, 3,4-diaminopyridine, eseridine, and galantamide, including pharmaceutically acceptable salts of those of the aforementioned compounds which are able to form salts with organic or inorganic acids.

3. The method of claim 1, wherein the CEI inhibitor is administered perorally.

4. The method of claim 1, wherein the CEI is administered perorally for preferred absorption through the oral mucosa.

5. The method of claim 1, wherein the CEI is administered in the form of a composition for controlled release or in the form of a device for controlled release, said composition or device being adapted for temporary retention within the oral cavity of said patient.

6. The method of claim 1, wherein the CEI is administered topically in the form of an ointment or in a form suitable for transdermal or transmucosal absorption in combination with a protective patch.

7. The method of claim 6, wherein the transdermal administration is to the submandibular region, the thyroid region, a ventrolateral region of the neck or a lateral facial region.

8. The method of claim 1, wherein the CEI is administered of from 0.1 to 2.500 mg over a sleeping period.

9. A method for treating snoring, sleep apnea and other forms of sleep disordered breathing, comprising administration to a patient a therapeutically effective dose of an acetyl choline esterase inhibitor (CEI) over an appropriate period of time substantially coinciding with the period of sleep of said patient, and of a therapeutically effective dose of a deep sleep promoting agent selected from anti-depressants, selective serotonin reuptake inhibitors, bensodiazepines, cyclopyrrolones, and antihistamines.

10. The method of claim 2, wherein the CEI inhibitor is administered perorally.

11. The method of claim 2, wherein the CEI is administered perorally for absorption through the oral mucosa.

12. The method of claim 3, wherein the CEI is administered perorally for absorption through the oral mucosa.

13. The method of claim 2, wherein the CEI is administered in the form of a composition for controlled release or in the form of a device for controlled release, said composition or device being adapted for temporary retention within the oral cavity.

14. The method of claim 3, wherein the CEI is administered in the form of a composition for controlled release or in the form of a device for controlled release, said composition or device being adapted for temporary retention within the oral cavity.

15. The method of claim 2, wherein the CEI is administered in the form of an ointment or in a form suitable for transdermal or transmucosal absorption in combination with a protective patch.

16. The method of claim 3, wherein the CEI is administered in the form of an ointment or in a form suitable for transdermal or transmucosal absorption in combination with a protective patch.

17. The method of claim 15, wherein the transdermal administration is to the submandibular region, the thyroid region, a ventrolateral region of the neck or a lateral facial region.

18. The method of claim 16, wherein the transdermal administration is to the submandibular region, the thyroid region, a ventrolateral region of the neck or a lateral facial region.

19. The method of claim 2, wherein the CEI is administered of from 0.1 to 2.500 mg over a sleeping period.

20. The method of claim 3, wherein the CEI is administered of from 0.1 to 2.500 mg over a sleeping period.

* * * * *

UNITED STATES PATENT AND TRADEMARK OFFICE
CERTIFICATE OF CORRECTION

PATENT NO. : 6,034,117
DATED : MARCH 7, 2000
INVENTOR(S) : JAN HEDNER & KRAICZI HOLGER

It is certified that error appears in the above-identified patent and that said Letters Patent is hereby corrected as shown below:

On the title page, bracket number 73 should be inserted and should read as follows:
Assignee:
A+ Science Invest AB
Goteborg, Sweden Signed and Sealed this Twenty-ninth Day of May, 2001

Attest:

NICHOLAS P. GODICI

Attesting Officer     Acting Director of the United States Patent and Trademark Office